United States Patent
Boonstra et al.

(10) Patent No.: US 8,256,054 B2
(45) Date of Patent: Sep. 4, 2012

(54) HYDRAULIC SYSTEM FOR DRIVING A MEMBRANE BRUSHHEAD WHICH INCLUDES BRISTLES MOUNTED THEREON

(75) Inventors: Meindert Hendrik Boonstra, Zwolle (NL); John Boersma, Zuidhorn (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 806 days.

(21) Appl. No.: 11/722,337

(22) PCT Filed: Dec. 20, 2005

(86) PCT No.: PCT/IB2005/054344
§ 371 (c)(1),
(2), (4) Date: Nov. 23, 2009

(87) PCT Pub. No.: WO2006/095222
PCT Pub. Date: Sep. 14, 2006

(65) Prior Publication Data
US 2010/0058547 A1     Mar. 11, 2010

Related U.S. Application Data

(60) Provisional application No. 60/638,056, filed on Dec. 21, 2004.

(51) Int. Cl.
*A61C 17/20* (2006.01)
(52) U.S. Cl. .......... 15/22.1; 433/118; 433/119; 433/216
(58) Field of Classification Search .................... 15/22.1; 310/14, 15, 17, 36; 433/118, 119, 216
See application file for complete search history.

(56) References Cited

U.S. PATENT DOCUMENTS

| | | | | |
|---|---|---|---|---|
| 3,518,766 | A * | 7/1970 | Burt | 433/86 |
| 5,934,908 | A * | 8/1999 | Woog et al. | 433/216 |
| 6,050,818 | A * | 4/2000 | Boland et al. | 433/118 |
| 6,058,541 | A * | 5/2000 | Masterman et al. | 15/28 |
| 6,102,700 | A * | 8/2000 | Haczek et al. | 433/118 |
| 6,164,967 | A * | 12/2000 | Sale et al. | 433/80 |
| 6,434,773 | B1 * | 8/2002 | Kuo | 15/22.1 |
| 6,644,878 | B2 * | 11/2003 | Hall et al. | 401/146 |
| 6,766,549 | B2 * | 7/2004 | Klupt | 15/22.2 |
| 7,120,960 | B2 * | 10/2006 | Hilscher et al. | 15/22.1 |
| 7,401,373 | B2 * | 7/2008 | Tybinkowski et al. | 15/29 |
| 8,046,861 | B2 * | 11/2011 | Joseph | 15/22.1 |
| 2005/0100867 | A1 * | 5/2005 | Hilscher et al. | 433/216 |
| 2005/0283928 | A1 * | 12/2005 | Grez et al. | 15/22.1 |

FOREIGN PATENT DOCUMENTS
DE   202005003515   6/2005

* cited by examiner

*Primary Examiner* — Mark Spisich
*Assistant Examiner* — Michael Jennings

(57) ABSTRACT

The toothbrush includes a handle portion which has a disc spring assembly driven by a solenoid coil. The upper end of a central shaft which extends from the solenoid is connected to a drive flexible membrane assembly which in operation moves back and forth under the positive action of the solenoid central shaft and the return action of the spring on the central shaft. The drive membrane acts on hydraulic fluid which extends through a stem portion of the toothbrush to the brushhead, which includes a movable brushhead membrane. The moving fluid acts on the brushhead membrane to move it.

8 Claims, 6 Drawing Sheets

HYDRAULIC SYSTEM FOR DRIVING A MEMBRANE BRUSHHEAD WHICH INCLUDES BRISTLES MOUNTED THEREON

CROSS REFERENCE TO RELATED APPLICATION

This application claims the benefit of U.S. provisional application Ser. No. 60/638,056 filed 21 Dec. 2004, which is incorporated herein by reference.

This invention relates generally to power toothbrushes, and more specifically concerns a power toothbrush which includes a movable/flexible membrane in the brushhead portion of the toothbrush. The membrane has toothbrush bristles mounted on the membrane.

Use of a movable/flexible membrane in a brushhead portion of a power toothbrush with bristles mounted thereon to achieve effective oral cleaning is shown in U.S. Patent Application No. 60/483,149, filed on Jun. 26, 2003, which is owned by the assignee of the present invention. The contents of that application are hereby incorporated by reference.

One important structural portion of such a membrane cleaning system is the drive mechanism/assembly for moving the membrane in the brushhead. It is important that such a drive system be reliable and provide enough power to adequately drive the flexible membrane. It is desirable that such a drive system be both inexpensive and easy to manufacture and fit conveniently into a conventional toothbrush Accordingly, the present invention is a power toothbrush, comprising a handle portion which includes a drive flexible membrane assembly, a spring assembly acting on the drive flexible membrane, a coil for moving the spring member and a driving/control system for driving the coil; and a stem/head portion which includes a brushhead at a remote end thereof, the stem/head portion extending from the handle portion, wherein the brushhead includes a brushhead membrane assembly, on which bristles are mounted, and wherein the stem/head portion includes a channel which is filled with fluid, the fluid extending between the drive membrane in the handle portion and the brushhead membrane assembly, transmitting in operation movement of the drive membrane to corresponding movement of movable portions of the brushhead membrane assembly, resulting in cleaning action for the teeth.

Those oral care devices which use a movable or flexible membrane at the remote end of the brushhead, with (or without) toothbrush bristles mounted on the membrane, to achieve desired oral cleaning include a drive train/system for moving the membrane with sufficient frequency and amplitude to achieve the cleaning.

Generally, the system shown and described herein includes a first flexible membrane, referred to herein as a drive membrane, at the top of a handle portion of the power toothbrush. The drive membrane moves in operation, resulting in corresponding movement of hydraulic fluid through the stem/head portion of the toothbrush to the brushhead which contains an inlay which includes a movable or flexible membrane, referred to herein as a brushhead membrane. The hydraulic fluid acts on the brushhead membrane, moving it in operation to achieve cleaning of the teeth.

Figure 1:
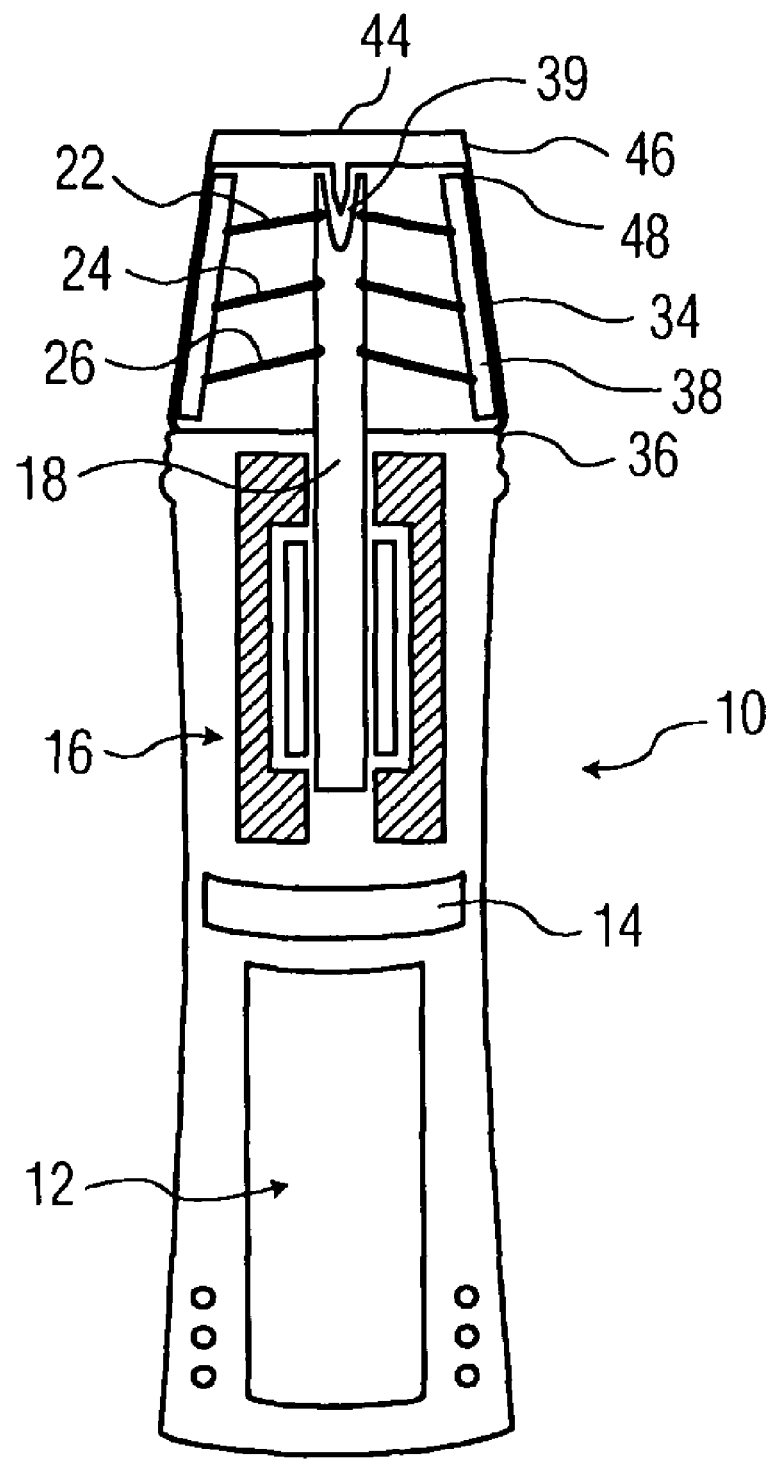
FIG. 1 is a cross-sectional view of a handle portion of a power toothbrush using the membrane drive system of the present invention.

The drive train for the oral care system, located in the handle, is shown in FIG. 1. FIG. 1 includes a power toothbrush handle 10, a battery 12 and an electrical driving/control circuit 14. Circuit 14, which is conventional, operates on a solenoid coil 16. The solenoid coil 16, when energized, pulls a central shaft 18 downwardly toward the bottom of the handle (away from the brushhead).

Figure 3:
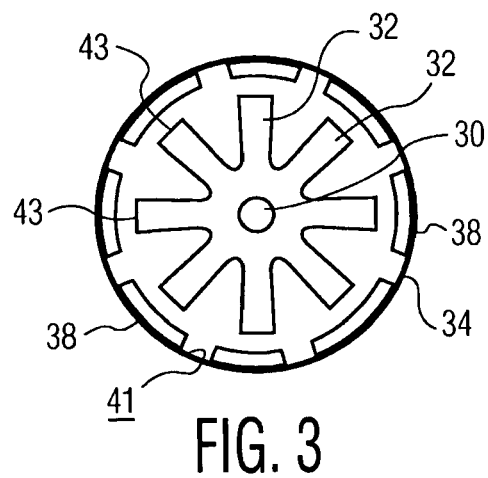
FIG. 3 is a lateral cross-sectional of the spring portion of FIGS. 2A and 2B.

At the upper end of central shaft 18, above the solenoid coil 16, are three vertically spaced concentric disc springs 22, 24 and 26. Each of the disc springs is fixedly attached to the central shaft 18. They could be metal or a polymer. In the embodiment shown, the three springs are separated sequentially by approximately 0.05-0.5 inches, although this spacing can be varied. FIG. 3 shows a top view of a disc spring. Each disc spring includes a central portion 30, which is secured to the central shaft 18, and a plurality of elongated, generally rectangular radial arms 32, which extend outwardly from the central portion 30. Surrounding the disc spring 22, 24, and 26 is a flexible, slightly conical, sheath 34. Flexible sheath 34 extends from the top edge 36 of the handle housing, to which it is attached, to a point a slight distance above the upper end 39 of central shaft 18.

A ring of spaced metal or plastic strips 38-38 are positioned around the internal surface 41 of the flexible sheath 34. The free ends 43-43 of the radial arms 32-32 of each disc spring are locked into place to a facing surface of strips 38 by means of barbs 45-45 on the facing surface or otherwise secured to the strips 38. The plurality of strips could alternatively be an expandable (flexible), somewhat conical cylinder.

Figure 2A:
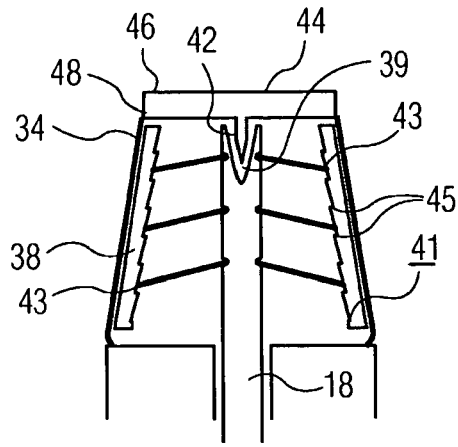
FIGS. 2A and 2B are cross-sectional views showing the operation of a spring portion of the membrane drive system of FIG. 1.
Figure 2B:
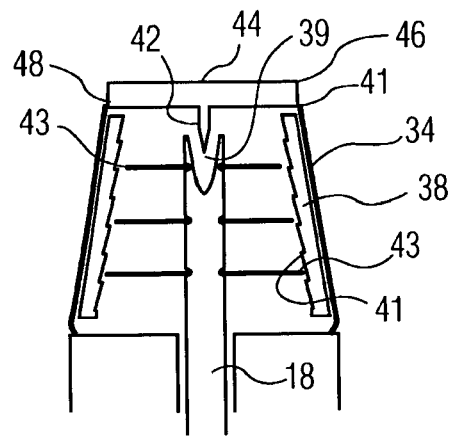

The upper end 39 of central shaft 18 is configured to mate with a depending center portion 42 of a drive flexible membrane 44, the peripheral edge 46 of which is connected with the upper edge 48 of flexible sheath 34. The central shaft 18 moves the drive membrane toward the brushhead, by the action of the springs, when there is no pulling action of the solenoid 16, as shown in FIG. 2A. The action of the solenoid pulls shaft 18 away from the brushhead, against the spring action. When solenoid 16 is energized, the diameter of the ring of strips, or the alternative cylinder, increases, pressing outwardly to and against the flexible sheath, as shown in FIG. 2B.

Figure 4:
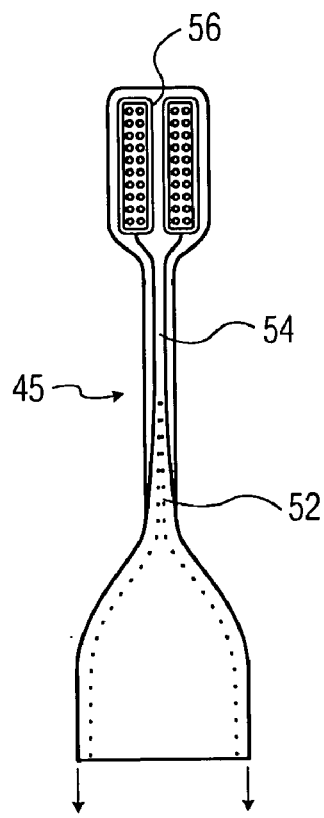
FIG. 4 is an elevational view showing the head portion of the toothbrush of FIG. 1, including the flexible membrane at the remote end of the brushhead.

Referring to FIG. 4, the above action and the resulting action of membrane 44 moves hydraulic fluid 52 in the stem/head portion 45 of the toothbrush, which is secured to the handle portion, such as by a screw-on connection. The hydraulic fluid 52 is moved back and forth through a channel 54 up into the brushhead of the toothbrush. The fluid 52 extends to a rear surface of a membrane insert 56 in the brushhead. The insert in the embodiment shown has a rigid plastic or metal base portion 60 in the embodiment shown and a polymer membrane portion 62. In the embodiment shown, the polymer membrane portion is divided into two adjacent longitudinal portions. The polymer membrane could be rigid, and mounted into the base portion 60 by hinge portions, as discussed in more detail below, or the membrane could be flexible, moving in and out in operation. Each of the portions has a plurality of bristle tufts (not shown) mounted therein and extending therefrom. In the rear surface of insert 56 is a valve opening 64, which can be used to fill the system with hydraulic fluid. It is also possible to use the embodiment shown without bristles.

Figure 6:
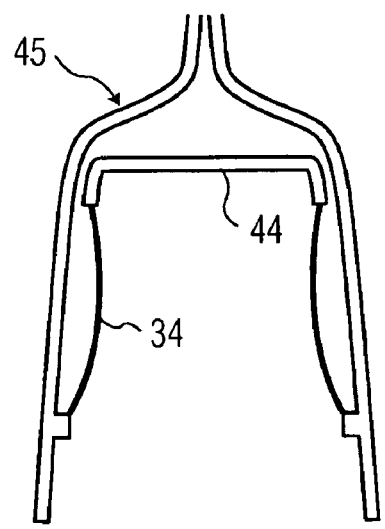
FIG. 6 is a cross-sectional view showing a replaceable portion of the assembly of FIGS. 1-4.

In the arrangement described above, referring to FIG. 6, the stem/head portion of the toothbrush, including the flexible sheath 34 and the drive membrane 44, is replaceable, i.e. removable from the handle portion, leaving the central shaft, the disc springs and the ring of strips or expandable cylinder in place, as shown in FIG. 6.

In operation, central shaft 18 moves up and down by action of the solenoid in one direction (down) when actuated and return action (up) by the disc springs when the solenoid coil is not actuated. The drive flexible membrane 44 moves accordingly, and hence, also the hydraulic fluid 52 in the stem/head portion of the device. The fluid, which extends up into the brushhead, moves the brushhead membrane 60. The solenoid 16 is actuated in such a manner to provide the proper frequency and desired amplitude of movement of the brushhead membrane and the bristles mounted thereon. The movement of the brushhead membrane produces a movement of the fluid in the mouth and action of the fluid to produce cleaning of the teeth and interdental cleaning, as discussed in the No. 60/483, 149 application in more detail.

Figure 7:
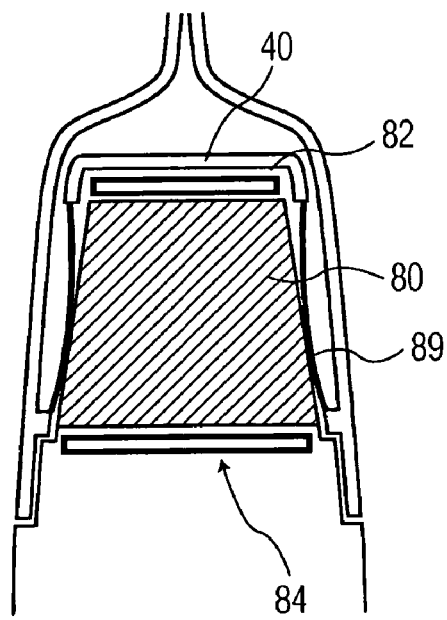
FIG. 7 is a cross-sectional view of an alternative embodiment of FIGS. 1-4.

An alternative drive train embodiment is shown in FIG. 7. This embodiment includes a slightly conical member 80 which can flex to some extent outwardly/inwardly. It is vibrated up and down by a piezoelectric assembly comprised of electrodes 82,84. This arrangement fits within a slightly conical, flexible surrounding membrane 88 having a drive membrane 90 secured to the top edge of the flexible membrane 88. In operation, the piezoelectric assembly will vibrate conical member 80 up and down, resulting in the outer wall thereof moving slightly inwardly and outwardly, forcing the wall of the surrounding membrane to move, as well as the flexible membrane 90. This results in a back-and-forth movement of the fluid in the brushhead stem acting on the membrane in the brushhead portion of the toothbrush.

Figure 5:
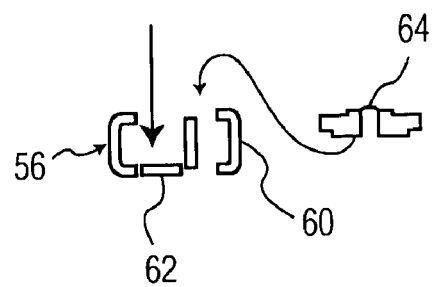
FIG. 5 is a cross-sectional view of the membrane inlay for the brushhead of the power toothbrush of FIG. 1.

FIGS. 8A-8D show in more detail a particular brushhead membrane arrangement. In this embodiment, which is similar to the embodiment of FIGS. 4 and 5, two polymer membrane portions 100, 102 are provided in an insert base member 104. The base member 104 includes two rigid side wall portions 106, 108 and a rigid third (mid)wall portion 110. Membrane portions 100 and 102 are mounted between the side wall portions 106 and 108, respectively, and midwall 110. The polymer membrane portions are mounted to move in the base member by flexible hinge sections 112-112 which extend the length of the membrane portions. Bristles extend from both moving membrane portions 100 and 102 as well as the rigid mid/wall portion 110.

Figure 8A:
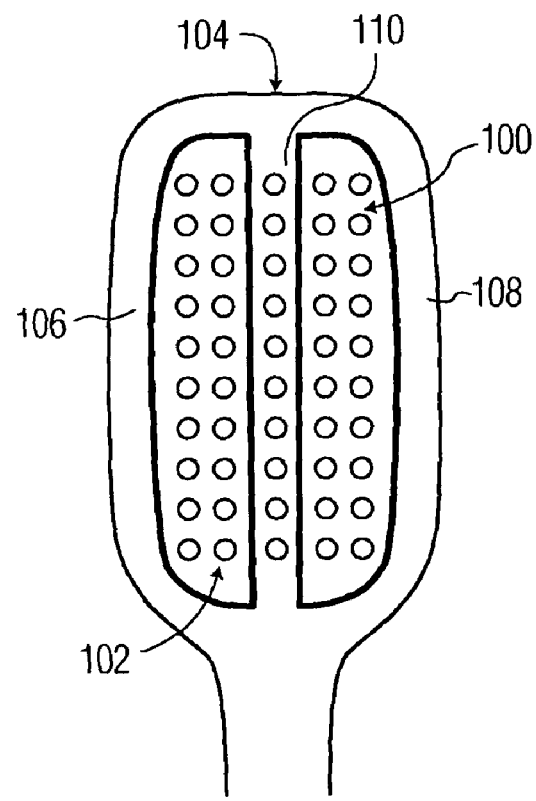
FIGS. 8A-8D show various views of the flexible membrane portion of the toothbrush shown in FIG. 4.
Figure 8B:
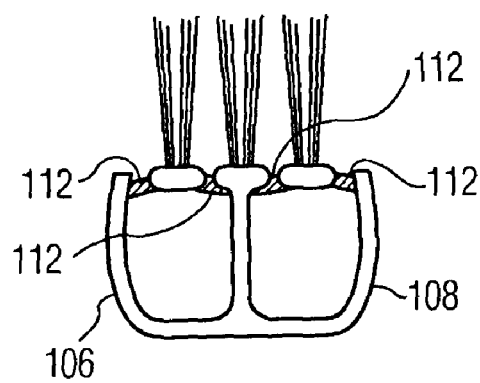
Figure 8C:
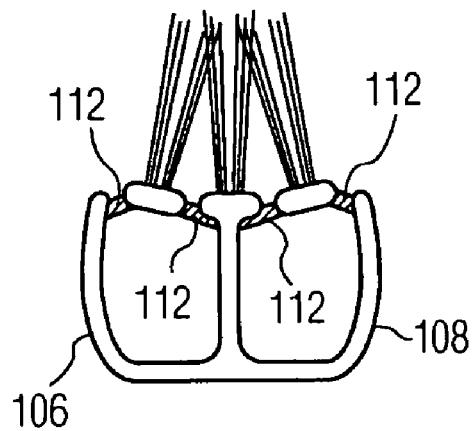
Figure 8D:
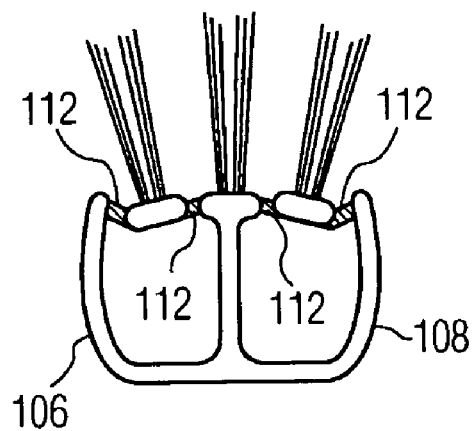

FIGS. 8B-8D show the movement of the membrane portions 100, 102 of the insert. The bristles on the two moving membrane portions 100 and 102 and the non-moving midwall portion are substantially vertical when there is no fluid pressure exerted within the insert (FIG. 7A). When fluid pressure is applied, by action of the drive train, the two moving membrane portions rotate somewhat inwardly, as shown in FIG. 7C, such that the bristles mounted thereon rotate toward the center bristles by virtue of the hinge structure 112. Correspondingly, when the fluid moves in the opposite direction, i.e. a "suction" action, the two moving membrane portions 100, 102 rotate slightly outwardly, as do the bristles thereon, as shown in FIG. 7D. The back-and-forth action of the bristles provides a cleaning action by the bristles interacting with the fluid in the mouth of the user.

As indicated above, while the embodiment shown include bristles mounted on the moving membrane portions of the insert, it is also possible to not have any bristles. In this arrangement, action is imparted to the fluid in the mouth by movable brushhead membrane portions. Hence, the scope of the present invention includes a bristleless brushhead membrane arrangement.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A power toothbrush, comprising: a handle portion which includes a drive flexible membrane assembly, a spring assembly acting on the drive flexible membrane assembly, a coil for moving the spring assembly and a driving/control system for driving the coil; and a stem/head portion which includes a brushhead at a remote end thereof, the stem/head portion extending from the handle portion, wherein the brushhead includes a brushhead membrane assembly, on which bristles are mounted, and wherein the stem/head portion includes a channel which is filled with fluid, the fluid extending between the drive membrane in the handle portion and the brushhead membrane assembly, transmitting in operation movement of the drive membrane to corresponding movement of movable portions of the brushhead membrane assembly, resulting in cleaning action for the teeth.

2. The toothbrush of claim 1, wherein the driving/control system includes a solenoid, acting on a movable central shaft, pulling it away from the brushhead when actuated, wherein the spring member is secured to the upper end of the central shaft.

3. The toothbrush of claim 2, wherein the spring member includes a plurality of disc springs which have a central portion connected to the upper end of the central shaft and a plurality of elongated arms which extend outwardly from the central portion and wherein the toothbrush further includes a flexible sheath at the upper end of the handle portion, the drive flexible membrane assembly connected to the top of the flexible sheath and an expandable assembly inboard of the flexible sheath to which the free edges of the elongated arms of the spring member are coupled, such that upon de-actuation of the solenoid, the spring member pulls the central shaft toward the brushhead into its rest position.

4. The power toothbrush of claim 3, wherein the stem/head portion of the toothbrush, including the drive flexible membrane assembly and the flexible sheath, are replaceable as a unit.

5. The toothbrush of claim 1, wherein the brushhead membrane assembly includes an insert member which has a rigid base portion and membrane portions mounted to be movable, wherein the toothbrush bristles are mounted on the movable membrane portions and a central portion of the base portion between the movable membrane portions.

6. A power toothbrush, comprising: a handle portion which includes a drive flexible membrane assembly, a spring assembly acting on the drive flexible member assembly, a coil for moving the spring assembly and a driving control system for driving the coil; and a stem/head portion which includes a brushhead at a remote end thereof, the stem/head portion extending from the handle portion, wherein the brushhead includes a brushhead membrane assembly, and wherein the stem/head portion includes a channel which is filled with fluid, the fluid extending between the drive membrane in the handle portion and the brushhead membrane assembly, transmitting in operation movement of the drive membrane to corresponding movement of movable portions of the brushhead membrane assembly resulting in cleaning action for the teeth.

7. A power toothbrush comprising:

a handle portion which includes a drive flexible membrane assembly, including a flexible sheath portion, an expandable element acting on the drive membrane assembly, a piezoelectric actuator assembly operating on the expandable element, and a driving control system for driving the piezoelectric actuator assembly; and a stem/head portion which includes a brushhead at a remote end thereof, the stem/head portion extending from the handle portion, wherein the brushhead includes a brushhead membrane assembly, and wherein the stem/head portion includes a channel which is filled with fluid, the fluid extending between the drive membrane in the handle portion and the brushhead membrane assembly, transmitting in operation movement of the drive membrane to corresponding movement of movable portions of the brushhead membrane assembly, resulting in cleaning action of the teeth.

8. The power toothbrush of claim 7, including bristles mounted on the brushhead membrane assembly.

* * * * *